US008388605B2

(12) United States Patent
Umemoto et al.

(10) Patent No.: US 8,388,605 B2
(45) Date of Patent: Mar. 5, 2013

(54) MANIPULATOR APPARATUS AND MEDICAL DEVICE SYSTEM

(75) Inventors: Yoshitaka Umemoto, Hachioji (JP);
Kazuhiko Takahashi, Hachioji (JP);
Tetsuo Nonami, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1162 days.

(21) Appl. No.: 12/260,437

(22) Filed: Oct. 29, 2008

(65) Prior Publication Data
US 2009/0112316 A1 Apr. 30, 2009

(30) Foreign Application Priority Data
Oct. 30, 2007 (JP) .................................. 2007-282144

(51) Int. Cl.
*A61B 17/00* (2006.01)
(52) U.S. Cl. .......................... 606/1; 606/130
(58) Field of Classification Search ................ 606/1, 130
See application file for complete search history.

(56) References Cited

U.S. PATENT DOCUMENTS

| | | | | |
|---|---|---|---|---|
| 4,833,624 A | * | 5/1989 | Kuwahara et al. | 700/249 |
| 4,835,710 A | * | 5/1989 | Schnelle et al. | 700/262 |
| 5,515,478 A | | 5/1996 | Wang | |
| 6,772,053 B2 | * | 8/2004 | Niemeyer | 700/302 |
| 7,035,716 B2 | * | 4/2006 | Harris et al. | 700/245 |
| 7,155,316 B2 | * | 12/2006 | Sutherland et al. | 700/248 |
| 7,725,214 B2 | * | 5/2010 | Diolaiti | 700/247 |
| 7,930,065 B2 | * | 4/2011 | Larkin et al. | 700/245 |
| 2008/0004632 A1 | * | 1/2008 | Sutherland et al. | 606/130 |
| 2008/0004634 A1 | * | 1/2008 | Farritor et al. | 606/130 |
| 2008/0065102 A1 | * | 3/2008 | Cooper | 606/130 |
| 2009/0024142 A1 | * | 1/2009 | Ruiz Morales | 606/130 |
| 2010/0004505 A1 | * | 1/2010 | Umemoto et al. | 600/106 |
| 2010/0204713 A1 | * | 8/2010 | Ruiz Morales | 606/130 |

FOREIGN PATENT DOCUMENTS

| | | |
|---|---|---|
| JP | 62-6306 A | 1/1987 |
| JP | H3-12709 | 1/1991 |
| JP | 06-342121 | 12/1994 |
| JP | H9-66056 | 3/1997 |
| JP | 2001-145638 A | 5/2001 |
| JP | 2004-129782 A | 4/2004 |

* cited by examiner

*Primary Examiner* — Henry M Johnson, III
(74) *Attorney, Agent, or Firm* — Scully, Scott, Murphy & Presser, P.C.

(57) ABSTRACT

A medical device system includes a manipulator including a plurality of joints, a parameter storing portion for storing joint parameters, including a largest available force, of each joint of the plurality of joints, a trajectory inputting portion for inputting, as a trajectory plan, trajectories for moving a distal end of the manipulator from a current position and attitude to a target position and attitude, a trajectory setting portion for setting a joint angle trajectory for each joint providing a largest available force from among joint angle trajectories which allow movement to the target position and attitude with a minimum number of driven joints based on a largest available force parameter for the each joint stored in the parameter storing portion and the trajectory plan.

6 Claims, 11 Drawing Sheets

MANIPULATOR APPARATUS AND MEDICAL DEVICE SYSTEM

CROSS REFERENCE TO RELATED APPLICATION

This application claims benefit of Japanese Application No. 2007-282144 filed on Oct. 30, 2007; the contents of which are incorporated by this reference.

BACKGROUND OF THE INVENTION

1. Field of the Invention

The present invention relates to a manipulator apparatus and a medical device system, and in particular to a manipulator apparatus having a plurality of joints driven efficiently in a manner dependent on a target treatment and to a medical device system which includes the manipulator apparatus.

2. Description of the Related Art

In recent years endoscopic surgery for performing various treatments inside a body cavity has become widespread. The endoscopic surgery is performed by opening an insertion hole in a body wall and inserting an endoscope and treatment instruments percutaneously into a body cavity through the insertion hole. This type of technique does not require a large dissection and is widely applied as a minimally invasive technique for cholecystectomy or resection of a part of the lung. To improve operability in this type of surgery, a master-slave type medical manipulator apparatus has been proposed.

Japanese Patent Application Laid-Open Publication No. H9-66056, for instance, discloses a medical manipulator system for use in surgery in which a plurality of medical manipulator apparatuses are used and which can cope quickly if a fault of some kind occurs in one or more of the manipulator apparatuses. The manipulator system provides a high degree of safety and operability, and allows a reduction in operating time and in the level of invasiveness to the patient.

When controlling multi-joint manipulators, inverse kinematic calculations are used to find target values for the attitude and position of manipulator distal end. In other words, when a trajectory plan is provided, inverse kinematic calculations are used to calculate joint angle trajectories for each joint. When, in the calculation of joint angle trajectories, the number of joints to be driven is large, overall driving error increases due to the compounding of errors at each joint. To deal with this problem, Japanese Patent Application Laid-Open Publication No. H3-12709 discloses a method which makes use of fuzzy inference to calculate the joint angle trajectories which allow the target values to be reached with the minimum number of driven joints.

In one type of endoscopic surgery even less invasive than conventional endoscopic surgery, treatment is performed using a medical instrument provided at a distal end portion of the endoscope. However, a treatment instrument which passes through the forceps channel of the endoscope and projects from distal end portion has poor operability, and so methods which make use of a miniature manipulator to increase the number of degrees of freedom and capabilities of the treatment instrument have been considered. Although it is difficult for such a miniature manipulator which projects from the distal end portion to have a complex structure due to size constraints, high levels of accuracy and efficiency are demanded. However, with this type of miniature manipulator apparatus, it is difficult to achieve both high accuracy and high efficiency.

A medical device system which makes use of one or more highly accurate and highly efficient miniature manipulators projecting from the distal end portion is also desired.

SUMMARY OF THE INVENTION

It is an object of present invention to provide a manipulator apparatus having a plurality of joints which are driven with high accuracy and high efficiency, and a medical device system equipped with the manipulator apparatus.

To achieve the object, the manipulator apparatus of the present invention includes a manipulator having a plurality of joints, a parameter storing portion for storing joint parameters, including a largest available force, of each joint of the plurality of joints; a trajectory inputting portion for inputting, as a trajectory plan, trajectories for moving a distal end of the manipulator from a current position and attitude to a target position and attitude; and a trajectory setting portion for setting a joint angle trajectory for each joint providing a largest available force from among joint angle trajectories which allow movement to the target position and attitude with a minimum number of driven joints based on a largest available force parameter for the each joint stored in the parameter storing portion and the trajectory plan. Further, the medical device system of the present invention includes the manipulator apparatus.

DETAILED DESCRIPTION OF THE PREFERRED EMBODIMENTS

The following describes embodiments of the invention with reference to the accompanying drawings.

<Overview of Medical Device System>

Figure 1:
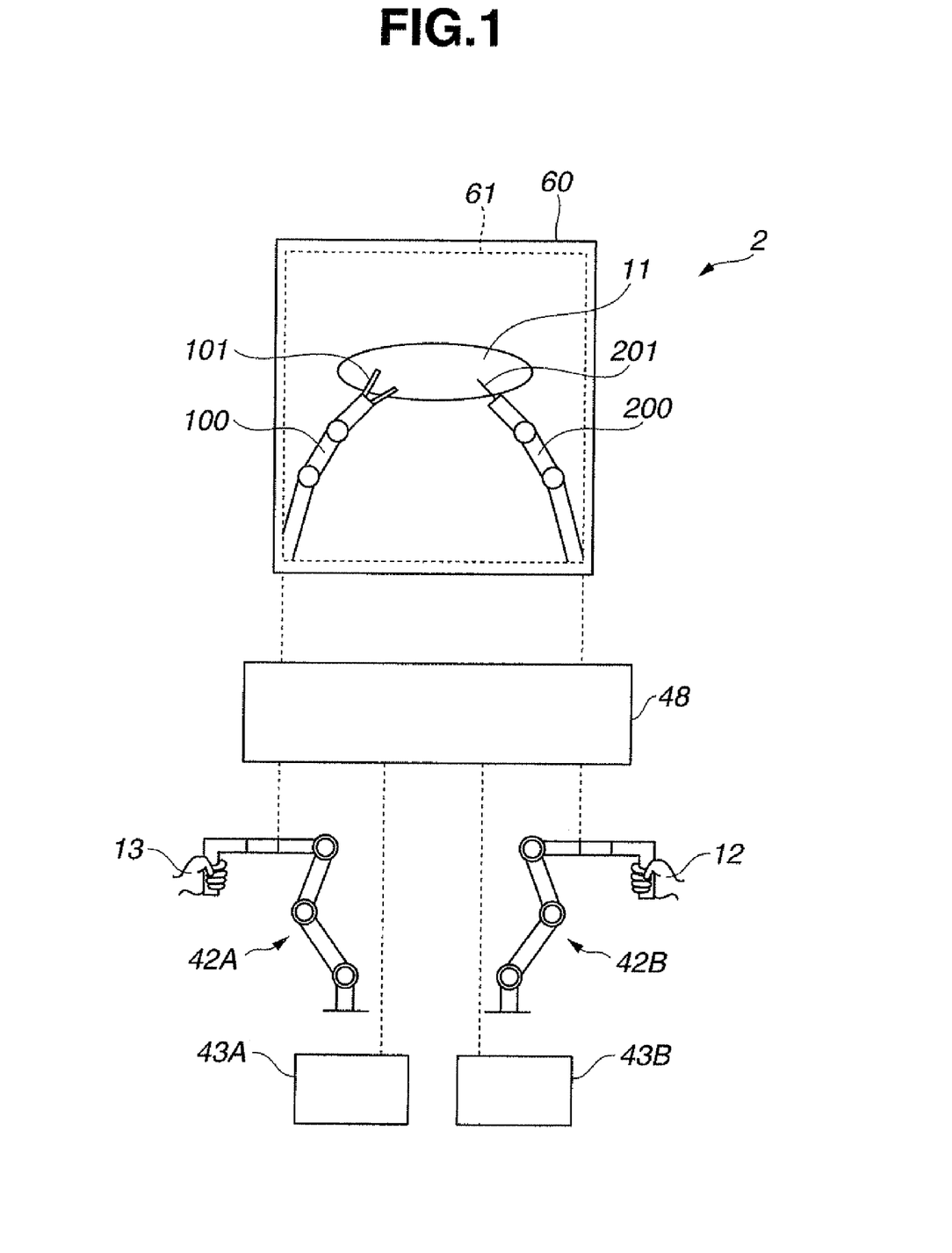
FIG. 1 is a schematic view for explaining an outline of a medical device system.

FIG. 1 is a schematic view for explaining an outline of a medical device system 2 of an embodiment of the invention. In FIG. 1, a display screen of a display apparatus 60, which is a display portion, displays a pickup image 61 of inside a living body 10 picked up using a CCD 51, which is an image pickup portion, of the endoscope apparatus 50 which is described in a later section. The pickup image 61 includes manipulators 100 and 200, each of which has two joints, for performing treatment on a diseased portion 11 within the living body 10. A hand arm is provided at a distal end portion 101 of the manipulator 100, and a knife arm is provided at the distal end portion 201 of the manipulator 200.

The operator operates the left and right master-slave apparatuses 42A and 42B using his or her left and right hands 12 and 13. The master-slave apparatuses 42A and 42B are trajectory inputting portion 42 for inputting trajectories for moving the distal end portions 101 and 201 of the manipulators 100 and 200 to a target position and attitude from a current position and attitude. A manipulator control apparatus 48 drives the manipulators 100 and 200 based on trajectory information inputted by the trajectory inputting portion 42.

Note that the medical device system 2 shown in FIG. 1 has a configuration which is basically the same as that of the present embodiment whether the manipulator apparatus has two manipulators, the manipulator apparatus has a single manipulator, or three or more manipulators.

Note also that the medical device system 2 includes degree-of-freedom selecting portions 43A and 43B for selecting degrees of freedom of the manipulators and limiting non-selected degrees of freedom. Although the manipulator of the present embodiment includes a plurality of joints and has a high number of degrees of freedom, in the medical device system 2 a manipulator with a fewer degrees of freedom may offer better operability, and safer and more reliable processing for some types of treatment. The operator is able to limit the number of degrees of freedom of the manipulators 100 and 200 according to the treatment by using the degree-of-freedom selecting portions 43A and 43B. The operations of the degree-of-freedom selecting portion 43 of are described in a later section.

Note that although FIG. 1 shows a master-slave type arrangement as the trajectory inputting portion 42, the invention is not limited to such a configuration, and another known type of inputting portion which permits input of desired trajectories, such as a keyboard, a touch pen or a joystick may be used.

Figure 2:
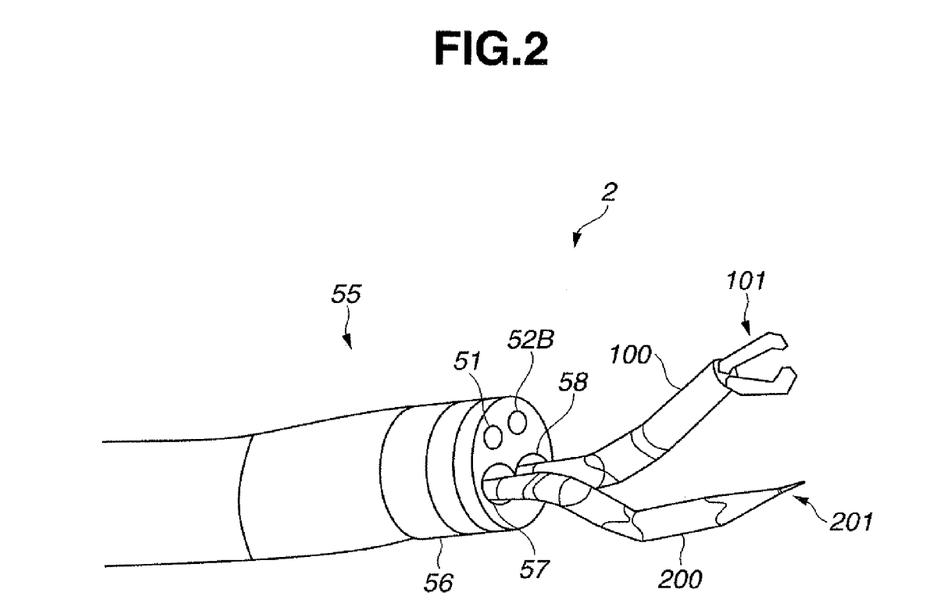
FIG. 2 is an external view showing an exterior of the medical device system.

FIG. 2 is an external view showing the exterior of the medical device system 2 of the present embodiment. In FIG. 2, the two manipulators 100 and 200 protrude from the forceps holes 57 and 58 of the distal end portion 56 of the endoscope 55. A CCD 51 which is the image pickup portion and an illuminating portion 52B which is an illuminating portion are provided in the distal end portion 56. Further, in the same way as in FIG. 1, a hand arm is provided at the distal end portion 101 of the manipulator 100 and a knife arm is provided at the distal end portion 201 of the other manipulator 200.

The manipulator of the present embodiment is a miniature manipulator for projection from the distal end portion of the endoscope, and, with a diameter of approximately 2 mm to 5 mm, is extremely compact. Hence, the manipulator differs from the majority of known manipulators, making it difficult to execute the target treatment unless the manipulator is driven efficiently.

<Structure of Manipulator>

Figure 3A:
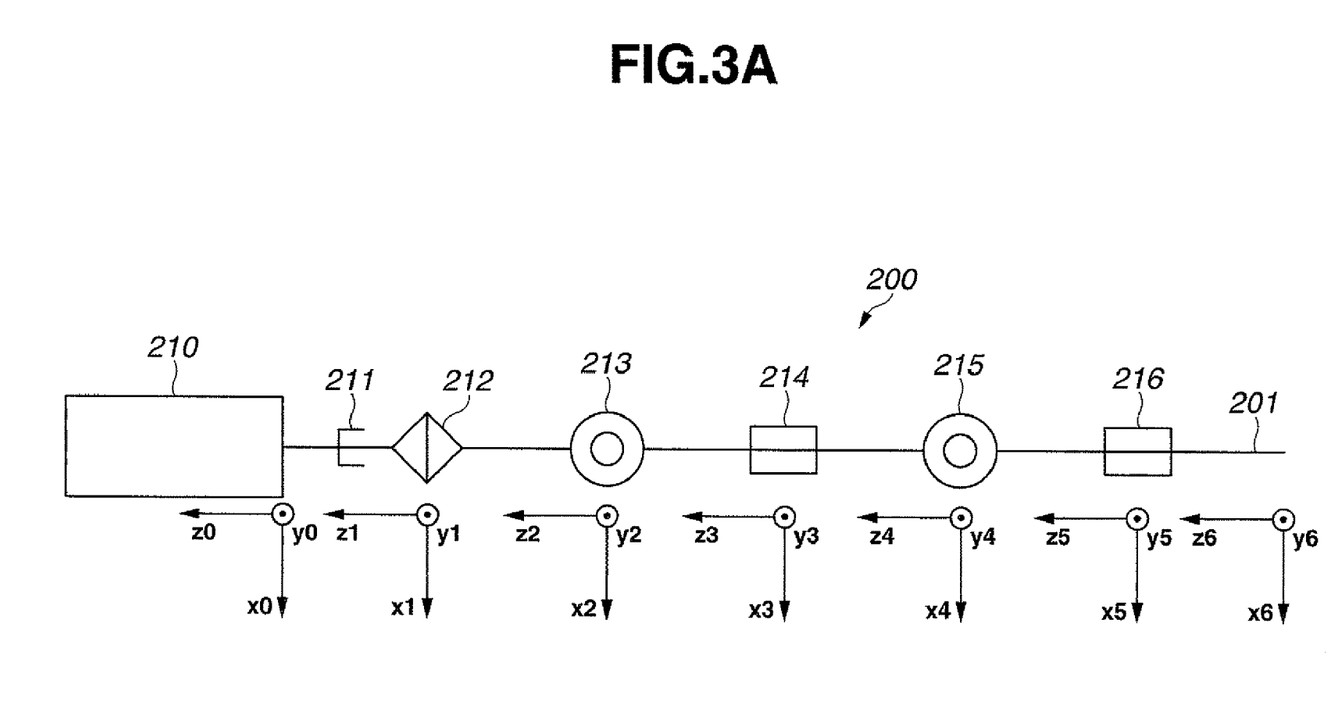
FIG. 3A is a diagram for explaining joint functions of a manipulator.
Figure 3B:
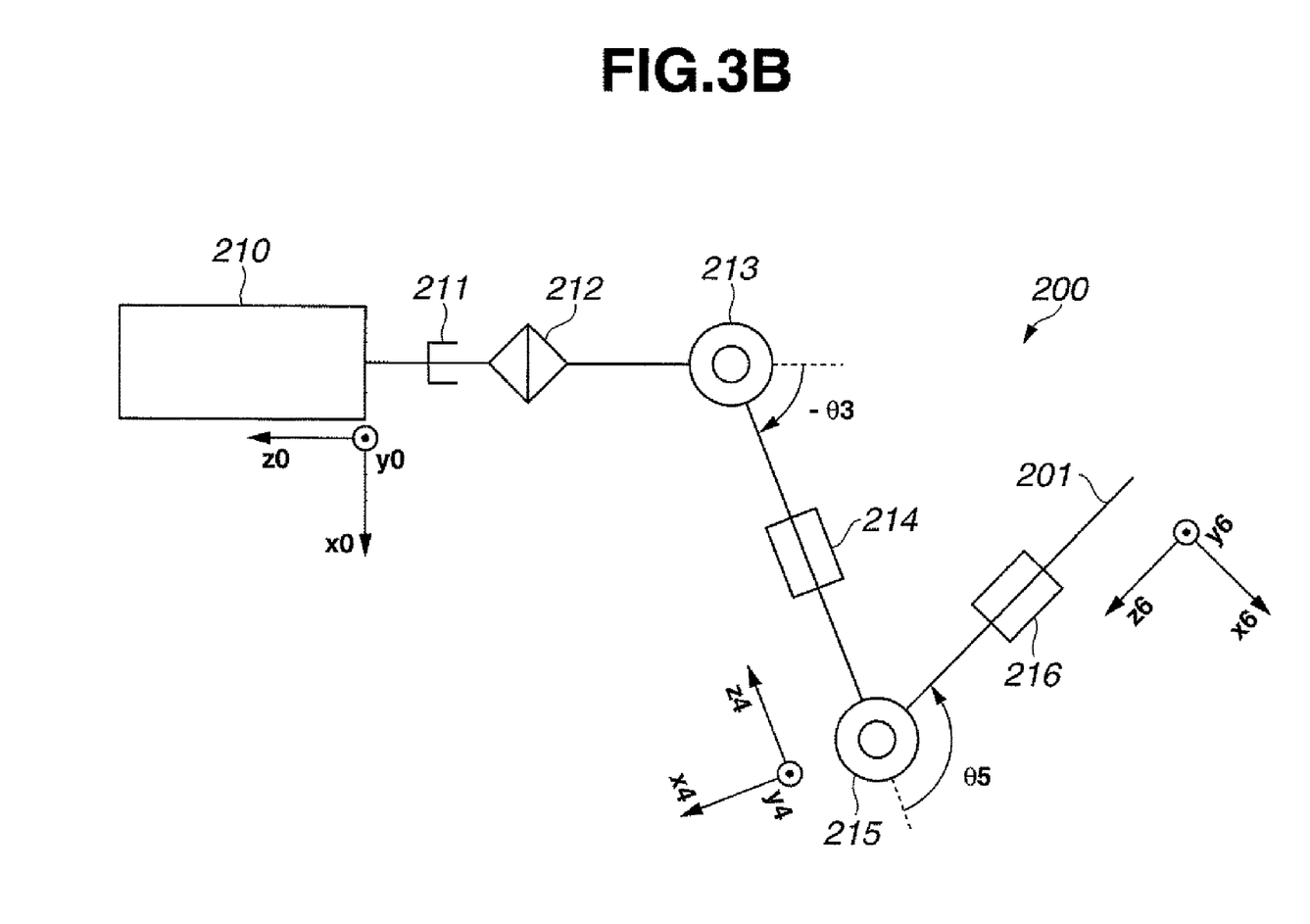
FIG. 3B is a diagram for explaining the joint functions of the manipulator.
Figure 4:
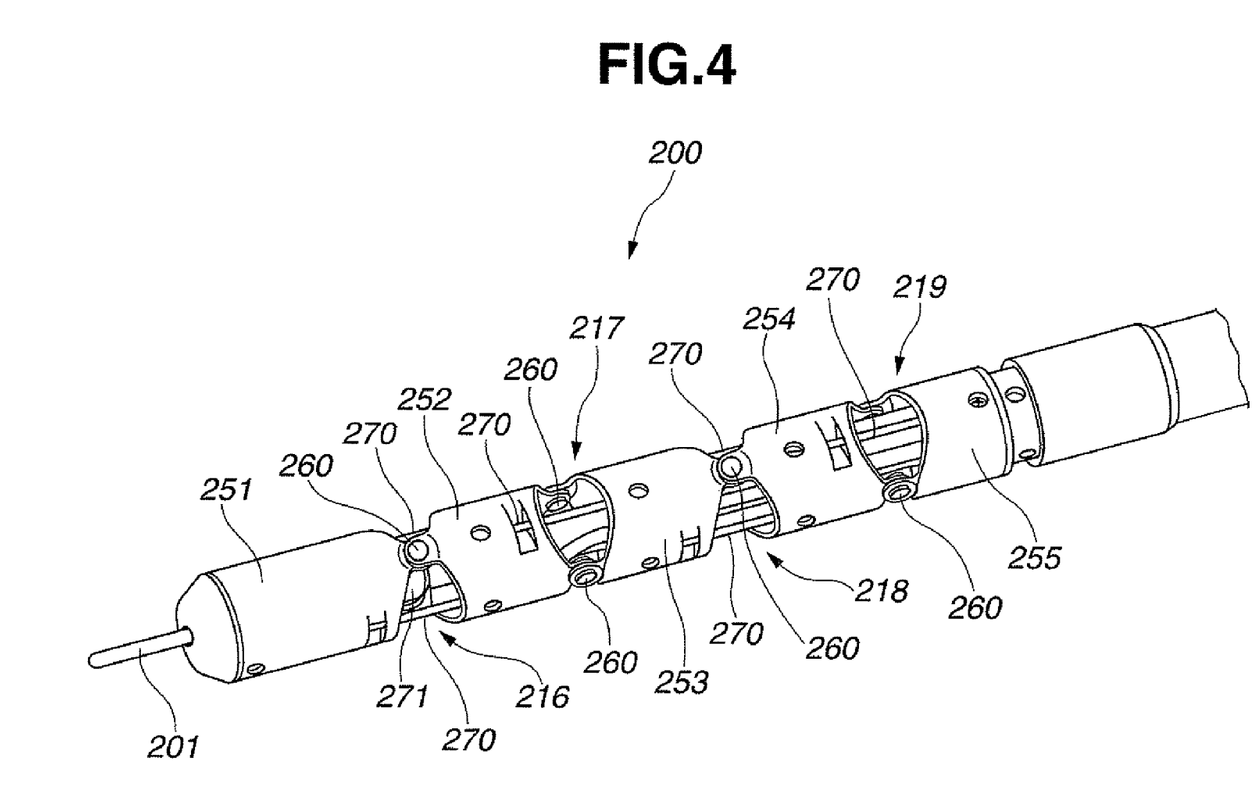
FIG. 4 is an external perspective view of the manipulator.
Figure 5:
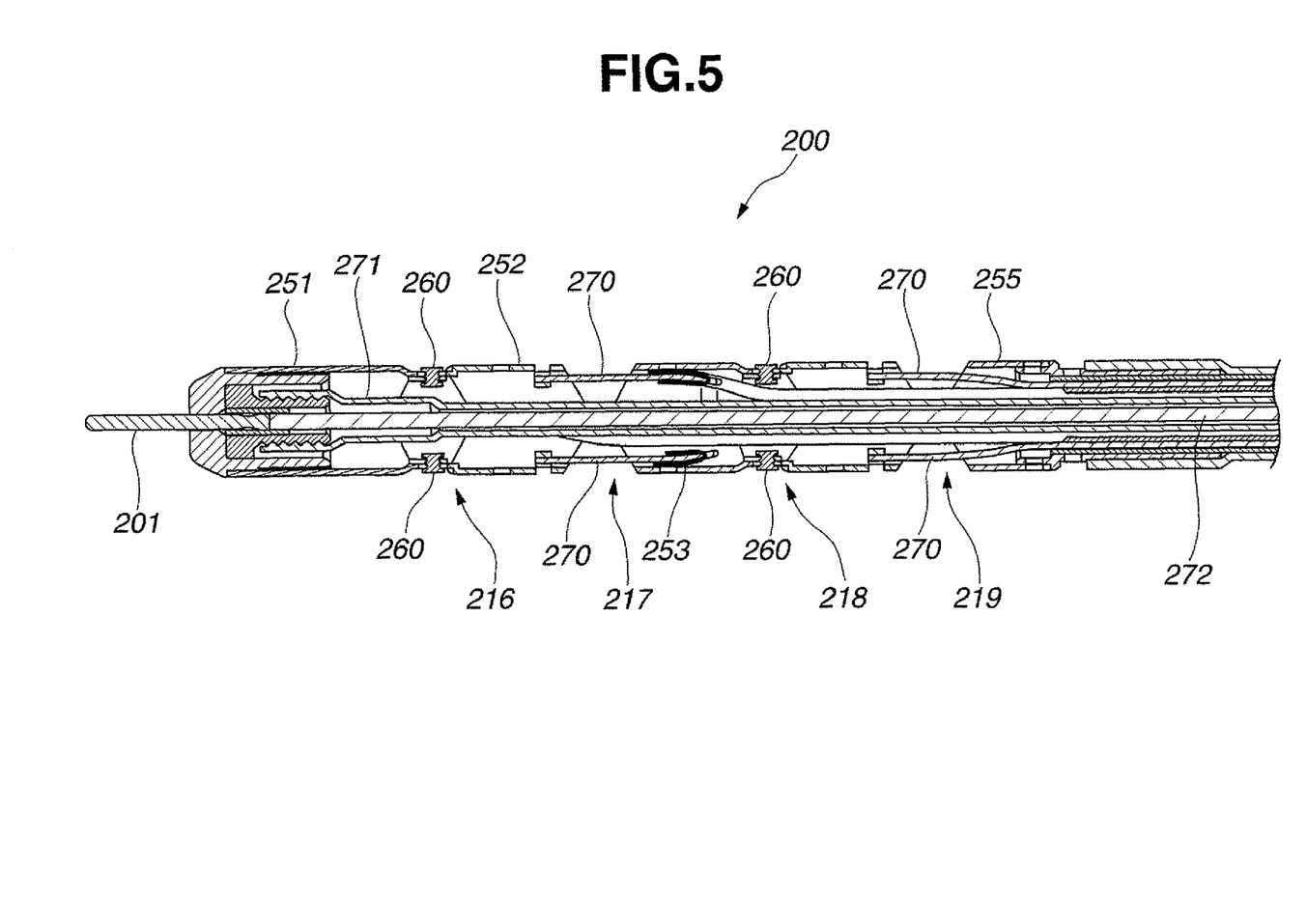
FIG. 5 is a cross-sectional view of the manipulator.
Figure 6:
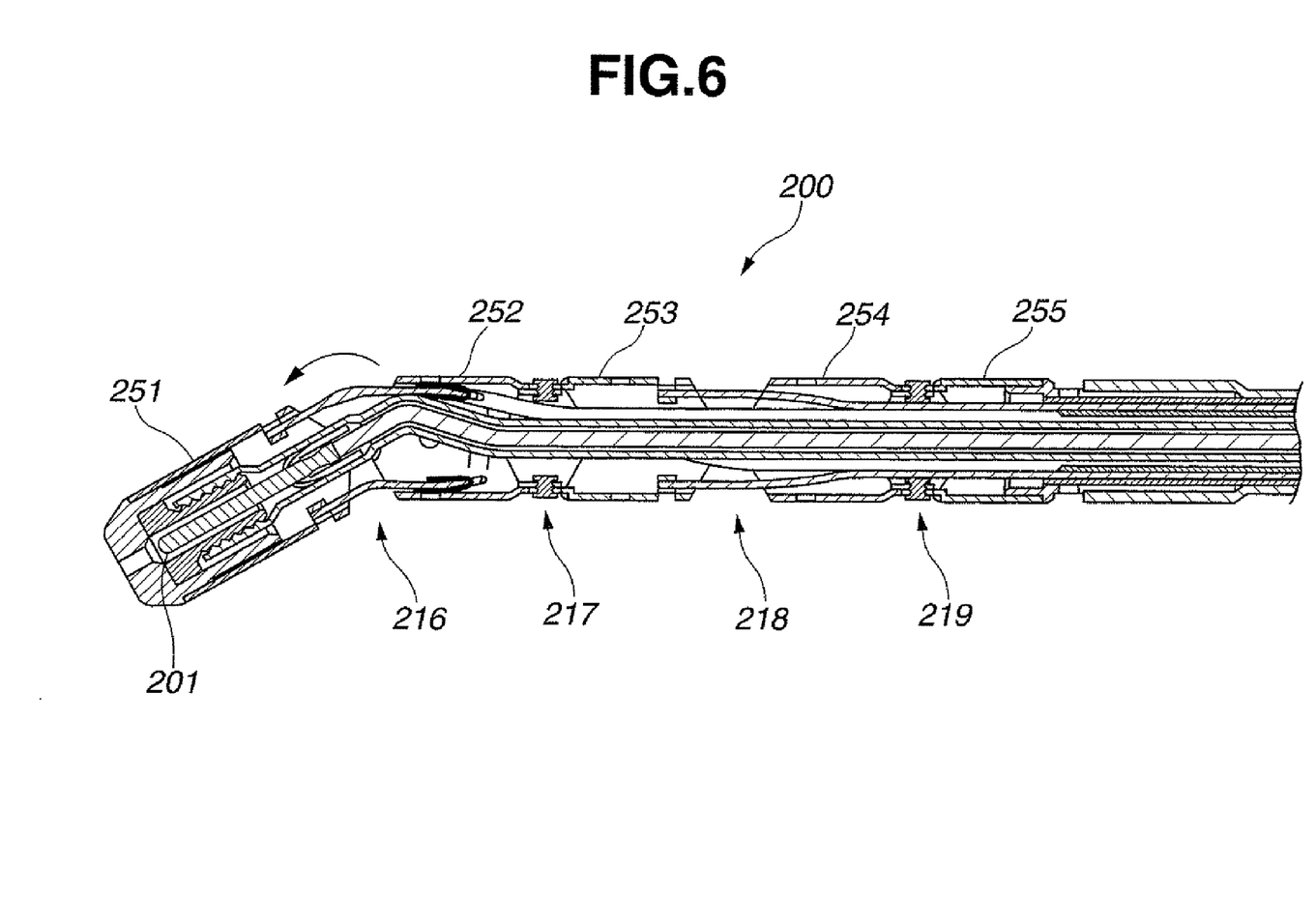
FIG. 6 is a cross-sectional view for explaining an operation of the manipulator.

The following describes the structure of the manipulator of the present embodiment with reference to FIG. 3 to FIG. 6. FIG. 3A and FIG. 3B are drawings for explaining functions of the joints of the manipulator 200. FIG. 4 is an external perspective view of the manipulator 200. FIG. 5 is a cross-sectional view of the manipulator 200. FIG. 6 is a cross-sectional view for explaining the operations of the manipulator 200.

FIG. 3A shows the joints of the manipulator 200. The manipulator 200 includes, in order starting with the manipulator proximal end portion 210 (coordinates: x0, y0, z0), a straight-line motion driving joint 211 (coordinates: x1, y1, z1), and a roll driving joint 212 (coordinates: x2, y2, z2) a yaw driving joint 213 (coordinates: x3, y3, z3), pitch driving joint 214 (coordinates: x4, y4, z4), yaw driving joint 215 (coordinates: x5, y5, z5) and pitch driving joint 216 (coordinates: x6, y6, z6), which are rotationally driven joints. The knife arm is provided at the distal end portion 201 of the manipulator 200.

FIG. 3B shows the joints manipulator 200 in a driven state. Here, the yaw driving joint 213 has introduced a bend of −3θ and the yaw driving joint 215 has introduced a bend of 5θ.

The manipulator 200 is able to move the distal end portion 201 from a current position and attitude to a target position and attitude by adjusting the joint angles of the plurality of joints. It is to be noted that the manipulator 200 has a higher number of degrees of freedom than are required to achieve the target position and attitude. In other words, since the manipulator 200 has a higher number of degrees of freedom than is demanded by the work, a plurality of joint angle trajectories exist for moving to the target position and attitude. Moreover, the accuracy and efficiency of the manipulator apparatus 1 differ according to which joint angle trajectories are selected.

The following describes the structure of the manipulator 200 in detail with reference to FIG. 4 and FIG. 5. As shown in the perspective view of FIG. 4, the manipulator 200 has five joint sections 251 to 255 joined by four joints 216 to 219. Each joint is fixed using rivets 260 in two locations and allows rotation in one direction. Thus, the manipulator 200 has two pitch driving joints 216 and 214 and two yaw driving joints 215 and 213. Each joint is fixed at two diagonal points with ends of a pair of angle wires 270. The joint sections 251 to 255 can be bent at the respective joints by operations on the angle wires 270 using a driving portion 23 (not shown). The manipulator 200 has a knife arm at the distal end portion 201 thereof, and position and attitude of the knife arm are changed by driving the manipulator 200.

FIG. 5 is a cross-sectional view of the manipulator 200 shown in FIG. 4. Within a central portion of the manipulator 200, an operation wire 272 of the knife arm is provided within a flexible tube 271 which is an insulator. The operation wire 272 allows high frequency electrical currents to be to be transmitted and is electrically connected to the knife arm.

FIG. 6 shows a state in which the knife arm is housed in the manipulator 200. In this state, the angle wires (not shown) are pulling the pitch driving joint 216, introducing a bend at the bending section 251 at the most distal end portion of the manipulator 200.

The manipulator apparatus 1 makes use of the angle wires to drive the manipulator 200 and can therefore have a structure which is simple, reliable and miniaturized.

<Configuration of Medical Device System>

Figure 7:
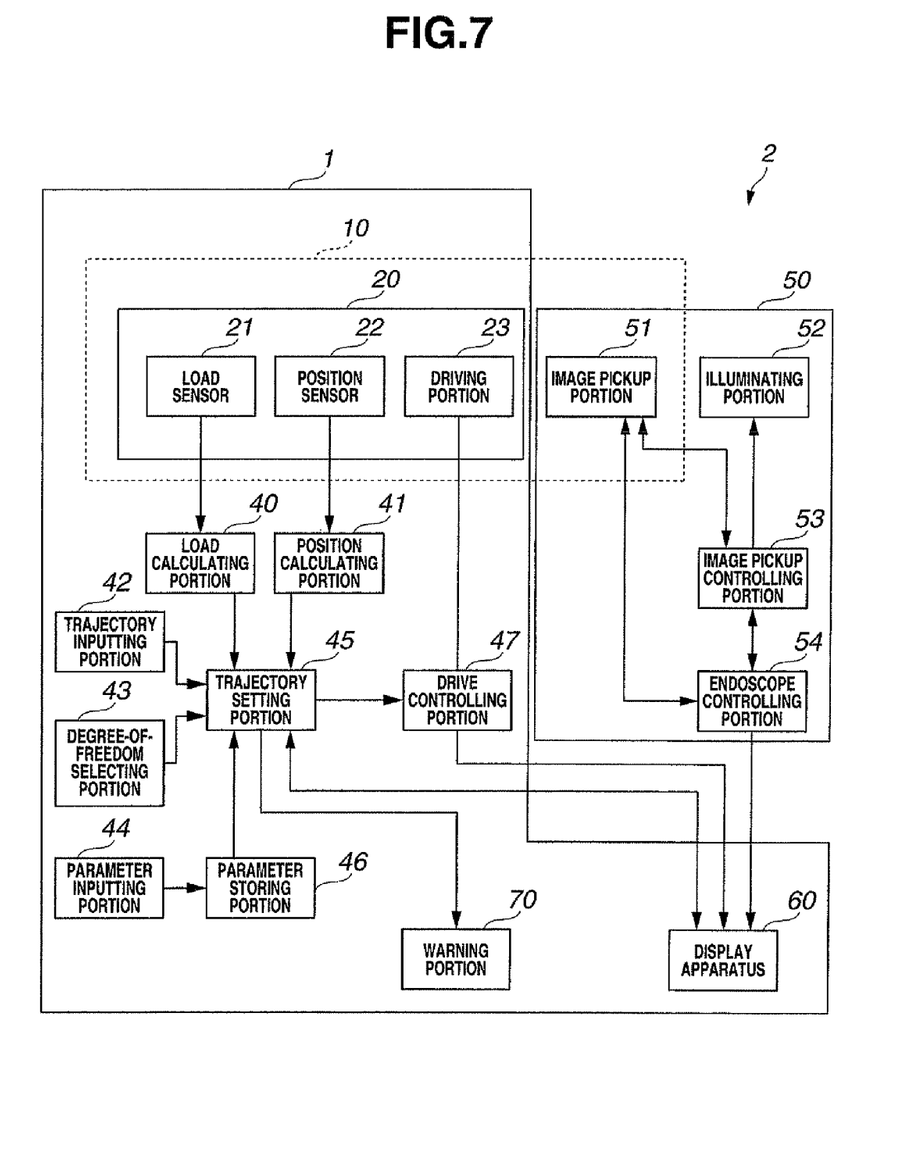
FIG. 7 is a block diagram of the medical device system.

The following describes a configuration of the medical device system 2 of the present embodiment with reference to FIG. 7. FIG. 7 is a block diagram showing a configuration of the medical device system 2 of the present embodiment. For the sake of simplicity, the following describes a medical device system 2 having a single manipulator 200. However, the basic configuration is the same when the medical device system 2 has a plurality of manipulator apparatuses 1. The only difference is the inclusion, in the case of the medical device system 2 having a plurality of manipulator apparatuses 1, of components for each manipulator apparatus.

FIG. 7 shows a configuration of a medical device system 2 featuring a manipulator (not shown) having a driving portion 20 for driving the manipulator within the living body 10. The manipulator includes a load sensor 21, a position sensor 22 and the driving portion 23.

The load sensor 21 is for detecting loads generated on each of the joints when the joints of the manipulator are driven to perform a desired operation. The load is expressed as torque (N/m) when a rotation driving joint is loaded and as force (N)

when a straight-line motion driving joint is loaded. One way of detecting the load when wire driving is used is to measure the tension in the wire. Another possibility is to detect the load with a strain gage or the like. Further, when the wire is driven using a motor, the load can be detected from the power consumption of the motor. Note that a new sensor does not necessarily have to be included in the manipulator. The components already present in the manipulator can, in some cases, be used to output load information to a load detecting portion 40.

The position sensor 22 is a sensor for detecting the position and attitude of each of the joints using a magnetic sensor or the like. Note that, like the load sensor 21, the position sensor 22 does not necessarily have to include a sensor in the manipulator. It is possible instead to detect the change in position and attitude of each joint caused by the driving portion 23 using an encoder and output the resulting position information to the position calculating portion 41.

A trajectory setting portion 45 sets the joint angle trajectory of each joint based on information from the position calculating portion 41, the trajectory inputting portion 42 and the degree-of-freedom selecting portion 43 and on joint parameters inputted from the parameter inputting portion 44 and the stored in parameter storing portion 46.

A drive controlling portion 47 drives the driving portion 23 of the joints of the manipulator in accordance with joint angle trajectories set by the trajectory setting portion 45.

The endoscope apparatus 50 includes the image pickup portion 51, which is a CCD or the like provided on a distal end portion of an insertion portion (not shown), the illuminating portion 52 for illuminating portions within the living body 10, an image pickup controlling portion 53 for performing processing and the like on the images picked up by the image pickup portion 51, and an endoscope controlling portion 54 for controlling the entire endoscope.

A display apparatus 60 displays the image picked up by the endoscope apparatus 50, and can be also used as a touch panel for inputting manipulator trajectories and the like.

Note that the load sensor 21, the load detecting portion 40, the position sensor 22 and the position calculating portion 41 need not be provided for all of the plurality of joints. In particular, the straight-line motion driving joint 211 and roll driving joint 212 may be driven by hand.

<Operations of Manipulator Apparatus>

Figure 8:
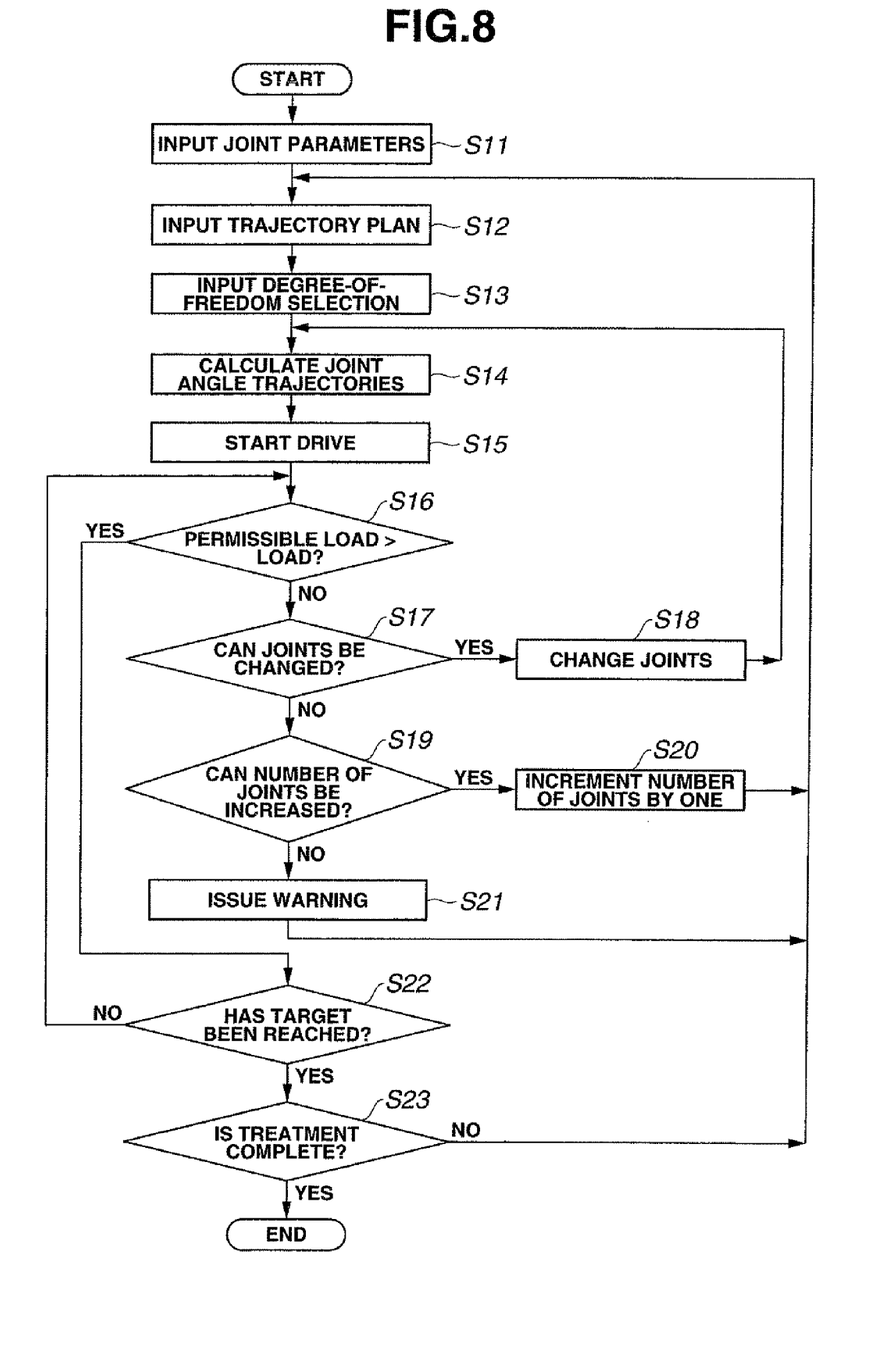
FIG. 8 is a flow chart for explaining the flow of operations of the manipulator apparatus.

The following describes operations of the manipulator apparatus 1 with reference to the flowchart of FIG. 8. FIG. 8 is a flow chart for explaining the flow of operations of the manipulator apparatus 1.

(Step S11)

The manipulator apparatus 1 receives input of joint parameters for each joint using the parameter inputting portion 44, and stores the inputted parameters in the parameter storing portion 46. Note that, if the joint parameters have been inputted in advance, there is no need to input parameters each time the manipulator apparatus is used.

Joint parameters are pieces of joint information necessary for driving the joints of the manipulator. In the medical device system 2, joint parameters may include DH parameters (initial coordinates, length, direction and the like), joint motion ranges (angle range, straight-line motion range, and the like), and joint operation accuracy (response speed and the like). The joint parameters in the medical device system 2 further include a largest available force parameter of the joints and a permissible load parameter for the joints.

The largest available force of a given joint is the maximum force which can be generated by that joint and, for rotationally driven joints, may be expressed in terms of torque (N/m) or driving motor electrical power (W). The permissible load of a given joint is the maximum load which can be applied to that joint. If a load which exceeds the permissible load is applied to any joint, there is a risk of damage to the joint or driving wires. For the rotationally driven joints, the permissible load is again expressed in terms of a torque or an electrical power value of the driving motor.

Note that the speed of the processing by the trajectory inputting portion 42 from step S12 onwards may be increased by arranging the joint parameters stored in the parameter storing portion 46 in order of available force or permissible load.

(Step S12)

A trajectory plan for moving the distal end of the manipulator from a current position and attitude to a target position and attitude is inputted using the trajectory inputting portion 42.

(Step S13)

Information for limiting the number of degrees of freedom of the manipulator is inputted by the degree-of-freedom selecting portion 43. The manipulator of the present embodiment has six degrees of freedom and can therefore be freely positioned with any attitude in three-dimensional space.

Figure 9:
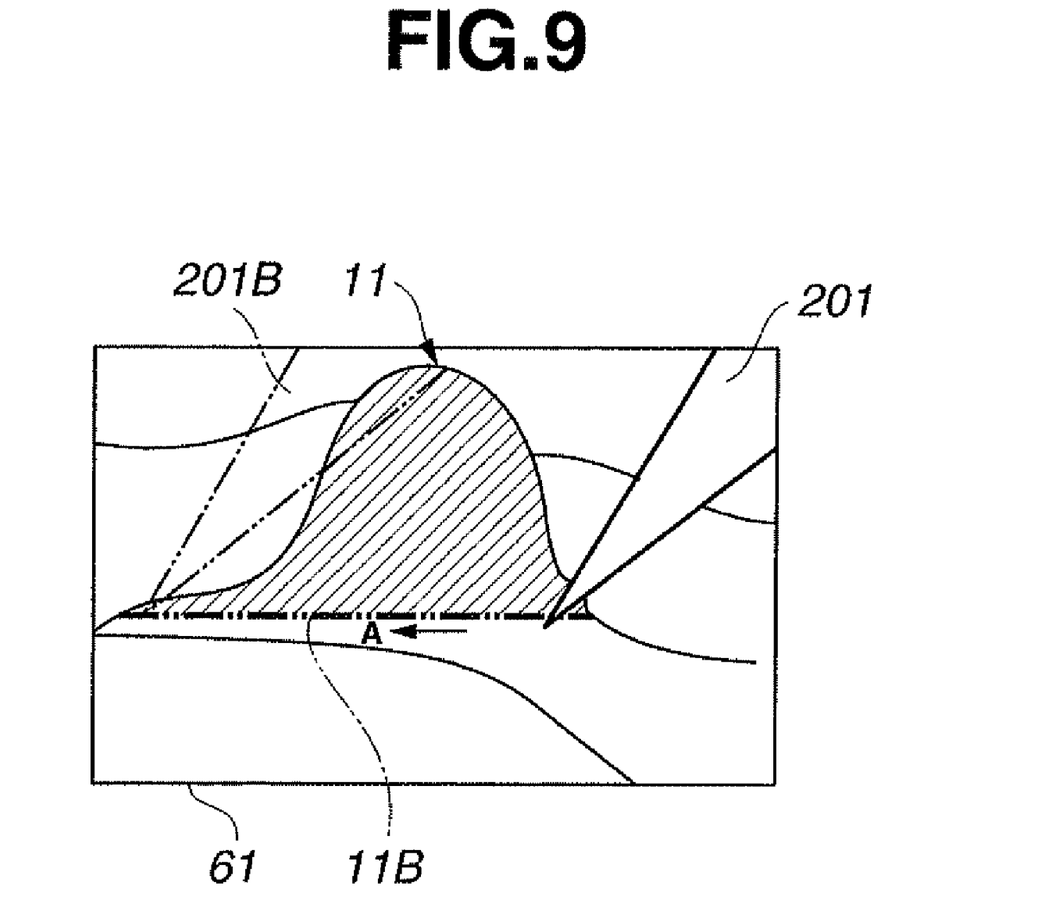
FIG. 9 is an endoscope pick up image showing a treatment using the manipulator.

FIG. 9 is a pickup image 61 from the endoscope and shows a treatment in which a scalpel at the distal end portion 201 of the manipulator 200 dissects a diseased portion 11. In this case, the distal end portion 201 is preferably moved from right left to left along the straight line 11B, as shown by the arrow A, to the position of the distal end portion 201B. However, unnecessary motion in the pitch and roll directions sometimes occurs, even if the operator was very careful when operating the master-slave apparatus (trajectory inputting portion 42).

In the case of the manipulator apparatus 1, however, the number of degrees of freedom in the pitch and roll directions can be limited when performing the above-described treatment using the degree-of-freedom selecting portion 43. When the distal end portion is a scalpel arm, the roll direction degree of freedom is not generally required.

The degree-of-freedom limiting information from the degree-of-freedom selecting portion 43 is used to cancel out inputs of the limited direction to the trajectory setting portion 45, which is described in a later section. Here, if the motion directions are expressed using vectors, to "cancel out" the input portion to remove the vector component in the limited direction.

By limiting the number of degrees of freedom using the degree-of-freedom selecting portion 43 the manipulator apparatus 1 is able to perform safer and more reliable processing.

(Step S14)

The trajectory setting portion 45 sets the joint angle trajectories of each joint based on the joint parameters and the trajectory plan. The trajectory setting portion 45 sets the joint angle trajectories providing the largest available force among the joint angle trajectories which allow movement to the target position and attitude with the minimum number of driven joints, based on the largest available force parameters for the joints stored in the parameter storing portion 46. Note that setting the joint angle trajectories to provide largest available forces does not necessarily mean to set the joint angle trajectories by selecting the joints which generate the largest forces but mean to set such joint angle trajectories as to generate the largest forces by giving precedence to the joints capable of generating the large force when selecting the joints.

Thus, in the manipulator apparatus 1 of the present embodiment, when the joint angle trajectories are set using inverse kinematic calculations, the number of joints is minimized to prioritize operation accuracy. The manipulator apparatus 1 of the present embodiment then selects, as a secondary priority, the joint angle trajectories which provide the largest available force.

Figure 10:
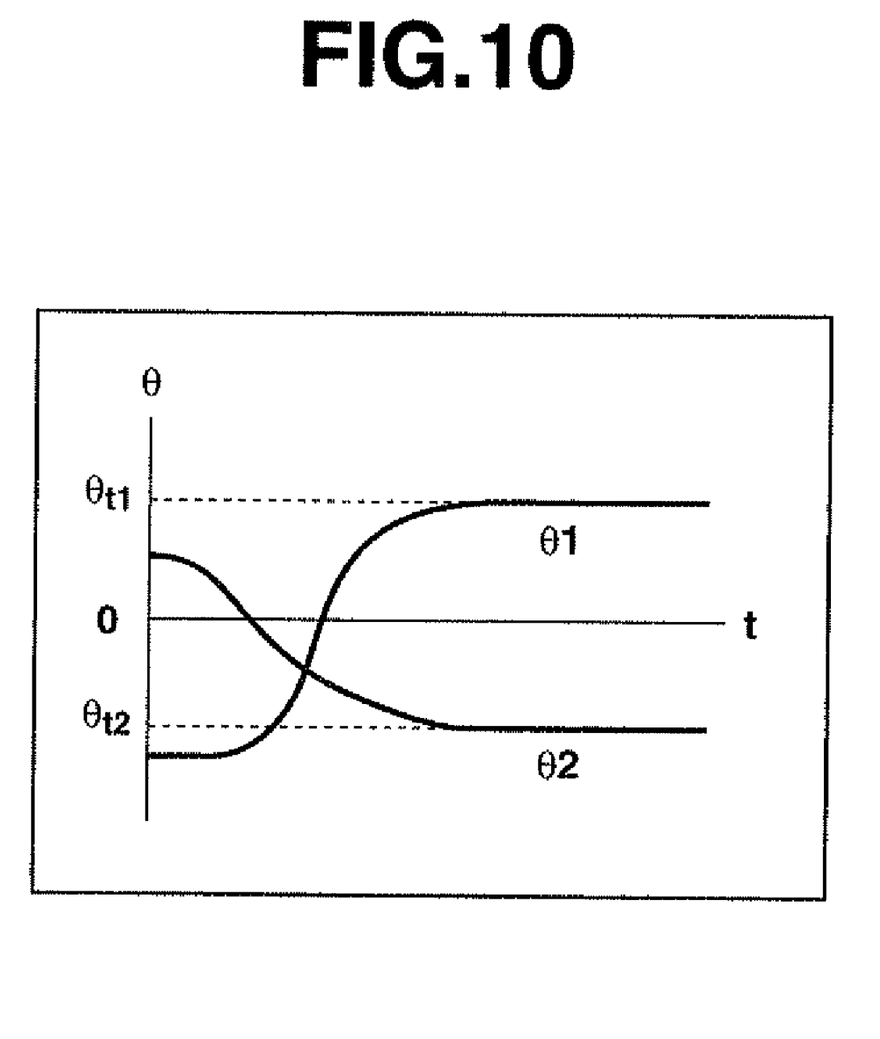
FIG. 10 shows an example of set joint angle trajectories.

FIG. 10 shows an example of the joint angle trajectories set by the trajectory setting portion 45. FIG. 10 shows the joint angle trajectory of two rotationally driven joints.

In the miniature manipulator apparatus for medical use, accuracy is most important. However, due to its small size, the manipulator can only generate small forces and is not always capable of executing the desired treatment.

Since the trajectory setting portion 45 sets the joint angle trajectory according to the above-described standards, the manipulator apparatus 1 of the present embodiment can perform safer and more reliable processing.

(Step S15)

The drive controlling portion 47 starts to drive the driving portion 23 of each joint in accordance with the joint angle trajectories set by the trajectory setting portion 45.

(Step S16)

When the driving of the driving portion 23 of the joints starts, a load is generated at each joint. When using the manipulator apparatus 1 of the medical device system 2, it is difficult to predict the loads on each joint before starting the treatment because the physical properties of the tissue to be treated, such as hardness, elasticity and the like, depend on the site of the treatment and vary from person to person.

Hence, when the driving portion 23 begins driving, the load detecting portion 40 calculates the load on each joint based on information from the load sensor 21. The trajectory setting portion 45 then compares the load on each joint with the permissible load parameter for each joint stored in the parameter storing portion 46, and, when the load on every joint is less than the permissible load, the driving portion 23 continues to drive the distal end portion of the manipulator until reaching the target position and attitude.

When, on the other hand, a load on any of the joints equals or exceeds the permissible load, the trajectory setting portion 45 performs the following processing to set new joint angle trajectories.

(Step S17)

When there are joints not currently being driven for which the permissible load parameter is larger than that of the joints currently in use (Yes), the trajectory setting portion 45 proceeds to step S18 and changes the joints to be driven. The joint angle trajectories are then recalculated.

When there are no joints not currently being driven for which the permissible load parameter is larger than that of joints currently in use (No), the trajectory setting portion 45 performs processing from step S19 onwards.

(Step S19)

In the case that not all of the joints are being driven (Yes), the trajectory setting portion 45 proceeds to step S20 and increments the number of joints to be driven by 1. The trajectory setting portion 45 then recalculates the joint angle trajectories.

(Step S21)

In step S19, when all of the joints are being driven (No), the trajectory setting portion 45 cannot move the manipulator distal end portion to the target position and attitude along the inputted trajectories, and therefore uses a warning portion 70 to issue a warning to inform the operator. The warning can make use of a known method such as a sound, vibration or a visual display on the display apparatus 60.

On receiving the warning, the operator can continue the treatment by inputting a new set of new trajectories.

(Steps S22 and S23)

In the manipulator apparatus 1, the drive controlling portion 47 drives the driving portion 23 of each joint in accordance with the joint angle trajectories set by the trajectory setting portion 45 until the manipulator distal end portion has moved to the target position and attitude. The manipulator apparatus 1 then continues to operate until a signal indicating the end of treatment is received in step S23.

The manipulator apparatus 1 of the present embodiment is highly accurate because only the minimum number of joints is driven. Moreover, the manipulator apparatus 1 generates a large force despite the miniature size of the manipulator. The manipulator can therefore be driven accurately and efficiently. The medical device system 2 including the manipulator apparatus 1 of the present embodiment can therefore drive the treatment instrument accurately, efficiently and reliably.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A manipulator apparatus comprising:
    a manipulator including a plurality of joints;
    a trajectory inputting portion for inputting, as a trajectory plan, trajectories for moving a distal end of the manipulator from a current position and attitude to a target position and attitude; and
    a manipulator control apparatus for driving the manipulator based on trajectory information inputted by the trajectory inputting portion, the manipulator control apparatus comprising:
        a parameter storing portion for storing joint parameters of each joint of the plurality of joints; and
        a trajectory setting portion for setting a joint angle trajectory to generate a largest force by giving precedence to the joints capable of generating the largest force when selecting the joints from among joint angle trajectories which allow movement to the target position and attitude with a minimum number of driven joints based on a largest available force parameter for the each joint stored in the parameter storing portion and the trajectory plan.

2. The manipulator apparatus according to claim 1, further comprising:
    a load detecting portion for detecting a load on the each joint, wherein
    based on a permissible load parameter for the each joint stored in the parameter storing portion, the trajectory setting portion sets a joint angle trajectory so that the load on the each joint does not exceed a permissible load on the each joint.

3. The manipulator apparatus according to claim 1, further comprising:
    a degree-of-freedom selecting portion for selecting a manipulator degree-of-freedom which is to be limited, wherein
    the trajectory setting portion cancels out an input of the trajectory inputting portion in a degree-of-freedom direction which has been limited.

4. A medical device system comprising:
    a manipulator apparatus comprising:
        a manipulator for use inside a living body, the manipulator including a plurality of joints;

a trajectory inputting portion for inputting, as a trajectory plan, trajectories for moving a distal end of the manipulator from a current position and attitude to a target position and attitude; and a manipulator control apparatus for driving the manipulator based on trajectory information inputted by the trajectory inputting portion, the manipulator control apparatus comprising:

a parameter storing portion for storing joint parameters, including a largest available force, of each joint of the plurality of joints; and a trajectory setting portion for setting a joint angle trajectory to generate a largest force by giving precedence to the joints capable of generating the largest force when selecting the joints from among joint angle trajectories which allow movement to the target position and attitude with a minimum number of driven joints based on a largest available force parameter for the each joint stored in the parameter storing portion and the trajectory plan; and an endoscope apparatus comprising an insertion portion having a distal end from which the manipulator projects.

5. The medical device system according to claim 4, further comprising:

a load detecting portion for detecting a load on the each joint, wherein based on a permissible load parameter for the each joint stored in the parameter storing portion, the trajectory setting portion sets a joint angle trajectory so that the load on the each joint does not exceed a permissible load on the each joint.

6. The medical device system according to claim 4, further comprising:

a degree-of-freedom selecting portion for selecting a manipulator degree-of-freedom which is to be limited, wherein the trajectory setting portion cancels out an input of the trajectory inputting portion in a degree-of-freedom direction which has been limited.

* * * * *